United States Patent [19]
Lux et al.

[11] 4,403,289
[45] Sep. 6, 1983

[54] METHOD AND DEVICE FOR COMPUTED TOMOGRAPHY

[75] Inventors: Peter W. Lux, Friedrichshafen, Fed. Rep. of Germany; Hendrikus F. Van Leiden; Johannes C. A. Op De Beek, both of Eindhoven, Netherlands

[73] Assignee: U.S. Philips Corporation, New York, N.Y.

[21] Appl. No.: 209,768

[22] Filed: Nov. 24, 1980

[30] Foreign Application Priority Data

Nov. 23, 1979 [NL] Netherlands ................... 7908545

[51] Int. Cl.³ .......................................... G06F 15/42
[52] U.S. Cl. ..................................... 364/414; 378/901
[58] Field of Search ................... 364/414; 250/445 T

[56] References Cited
U.S. PATENT DOCUMENTS 4,144,569  3/1979  Wagner ........................ 364/414
4,149,081  4/1979  Seppi ............................ 364/414
4,272,820  6/1981  Lux .............................. 364/414

Primary Examiner—Errol A. Krass
Attorney, Agent, or Firm—Jack E. Haken

[57] ABSTRACT

A computer tomography device in which the detectors are asymmetrically arranged with respect to the connecting line between the X-ray source, the center of rotation of the source, and the detectors, produce. The detector device produces an incomplete profile of measuring values which are supplemented with "zeros" during processing in order to form a number of measuring values of a complete profile. In order to avoid artefacts which are produced by the acute transients between measuring values and "zeros", a number of measuring values adjoining the acute transients are projected around the center of rotation and multipled by a factor so that from the zeros a smoothly increasing series of adapted measuring values is obtained.

4 Claims, 6 Drawing Figures

METHOD AND DEVICE FOR COMPUTED TOMOGRAPHY

The invention relates to a device and method for determining a radiation absorption distribution in a plane of a body.

BACKGROUND OF THE INVENTION

A device of this kind is known from Netherlands Patent Application No. 76.05.687 in which it is disclosed that the resolution of the radiation absorption distribution to be determined can be substantially doubled by asymmetrical positioning of the detector device with respect to the centre of rotation. However, it has been found that artefacts occur in an absorption image obtained by means of the device described in said Patent Application. These artefacts also occur if the centre of rotation is not situated on a measuring path at the edge of the beam, but on a measuring path inside the beam, in which case the body to be examined is only partly irradiated. These artefacts are to be attributed to the fact that the measuring signals are a part of a series of measuring signals which would be obtained if the body were completely irradiated and the radiation having passed through the body were measured. Each interrupted series of measuring signals applied by the detector device for each radiation source position, consequently, includes a sudden transition from a finite measuring signal to the value zero. These transitions actually contain information which is not present in the body and which is thus artificially produced and falsifies the image of the radiation absorption to be reconstructed.

SUMMARY OF THE INVENTION

The invention has for its object to provide a device in which the occurrence of artefacts due to the measurement of radiation absorption by means of a detector device which is asymmetrically situated with respect to the centre is avoided.

To this end, the device in accordance with the invention is characterized in that the device comprises means for the adaptation of measuring signals, said means multiplying a measuring signal associated with a first measuring path, situated between a measuring path extending through the centre of rotation and the extreme measuring path nearest to the centre of rotation, by a factor f, a measuring signal associated with a second measuring path which is situated as a mirror-image of the first measuring path with respect to the centre of rotation being multiplied by a complementary factor (1-f), the factor f has the value 0.5 for the measuring signal associated with the measuring path extending through the centre, the value 0 for the measuring signal associated with the extreme measuring path situated nearest to the centre, and decreasing monotonicly therebetween from the value 0.5 to the value 0 as a function of the distance from the centre of rotation.

When the measuring signals are processed by the means in accordance with the invention, all sudden transitions to zero are avoided. Furthermore, the variation of the multiplication factor is chosen so that, if a measuring signal is multiplied by a first factor and a measuring signal obtained after rotation of the radiation source and the detector device along the same but oppositely directed measuring path is multiplied by a second factor, the second factor is the "complement" of the first factor (f and (1-f), respectively).

The invention will be described in detail hereinafter, by way of example, with reference to the drawing which shows an embodiment of a computer tomography device.

IN THE DRAWINGS

FIG. 1 diagrammatically shows the computer tomography device in accordance with the invention, FIG. 2 is a detailed view of the radiation source and detector arrangement with respect to their centre of rotation FIGS. 3a, b, c each show a diagram of a group of measuring values supplied by the detector device of FIG. 1, and FIG. 4 shows a part of the processing device of FIG. 1.

DESCRIPTION OF THE PREFERRED EMBODIMENT

Figure 1:
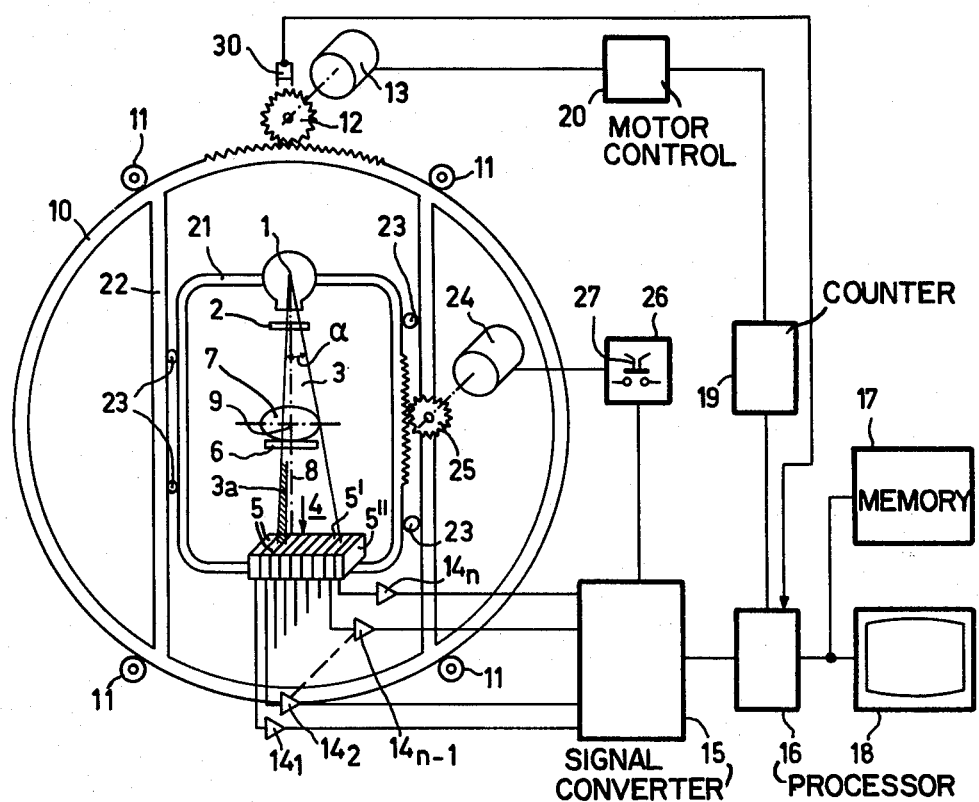

A computed tomography device as shown in FIG. 1 comprises a radiation source 1 which is preferably an X-ray source but which may also be a radioactive isotope such as Am 241. Using a diaphragm 2, the radiation emitted by the radiation source 1 is collimated to form a diverging radiation beam 3 which is situated in the plane, the thickness of the radiation beam 3 perpendicular to the plane being, for example, from 3 to 25 mm, its divergence in the plane being determined by the angle $\alpha$. The radiation beam 3 is incident on a detector array 4 which consists of separate detectors 5 which measure the radiation and which define measuring paths 3a (only one is shown). The distance between the individual detectors 5 determines the spatial accuracy with which an object 7 arranged on an object table 6 is scanned. The detector array 4 is asymmetrically positioned with respect to a measuring path extending through the centre of rotation 9 (only the centre line 8 is shown) and comprises, for example, 300 detectors 5, the centre-to-centre distance between two neighbouring detectors 5 amounts to from one to a few millimeters. For the detector device use can alternatively be made of an elongate gas-filled ionization chamber in which electrodes which detect separate zones are arranged in a row. The object 7 extends perpendicular to the plane of the radiation beam 3 in the longitudinal direction of the rotary axis through the centre of rotation 9 which is situated within the object 7. The object table 6 is displaceable in the longitudinal direction, so that several parallel layers of the object 7 can be examined. A circular supporting frame 10 is rotatably journalled around the centre of rotation 9, so that the object 7 can be irradiated in a multitude of directions. The rotation of the supporting frame 10 is guided by means of bearings 11 and is realized by means of drive means such as a gearwheel 12 which is driven by a motor 13. The rotation of the supporting frame 10 may be continuous or intermittent, the object 7 being flashed by the radiation source 1 after each step in the latter case.

After a first irradiation of the object 7 by means of the radiation source, the measuring signals processed by a signal converter 15 are counted by a counter 19. As soon as the number of measuring signals counted corresponds to the number of detectors 5, a control circuit 20 is activated which briefly drives the motor 13, thus moving the radiation source 1 to a next radiation source position by rotation of the supporting frame 10. In this radiation source position, the object 7 is irradiated again, etc. The angular rotation θ between the successive irradiation operations is determined by means of a sensor 30 which counts the teeth of the gearwheel 12. The pulses generated by the sensor 30 are applied to the processing device 16, so that, in combination with the data concerning the geometrical construction of the radiation source 1 and the detector array 4 which are stored in the processing device 16, the coordinates of all measuring paths can be determined.

It has been found that the distance between the radiation source 1 and the object 7 should preferably be adaptable to the largest dimension of the object 7. To this end, the system formed by the radiation source 1 and the detector array 4 is mounted on a support 21 which can be displaced along the guide rails 22 on the bearing 23 and by means of a gearwheel drive 25 coupled to a motor 24. A control circuit 26 can be operated, for example, by means of a manual switch 27; the circuit 26, however, any alternatively be automatically operated. Before the start of a first irradiation, the measuring signals of two detectors 5' and 5" are applied to the control circuit 26 via the signal converter 15. The support 21 is displaced so that the measuring signal of the detector 5" becomes maximum, whilst the measuring signal of the detector 5' has a slightly lower value. The detector 5" then receives radiation which completely bypasses the object 7, whilst the radiation detected by the detector 5' passes (partly) through the contour of the object 7, and is thus somewhat attenuated. After the support 21 has reached the desired position, the control circuit 26 is locked in order to keep the distance between the radiation source 1 and the centre of rotation constant during all subsequent irradiations the successive radiation source positions.

The measuring signals generated by the amplifiers 5 are amplified by the detectors $14_1, 14_2, \ldots, 14_{n-1}, 14_n$ and applied to a signal converter 15 in which the measuring signals are logarithmated in known manner, for example, on the basis of the logarithm tables stored in the signal converter 15, after which they are digitized. Via the output of the converter 15, the converted measuring signals are stored in a memory 17. A processing device 16 converts the measuring signals in known manner into a radiation absorption distribution which is represented as a reconstruction image in a matrix of elements, said distribution being stored in the memory 17 again. The radiation absorption distribution can be displayed on a display device such as a monitor 18.

Figure 2:
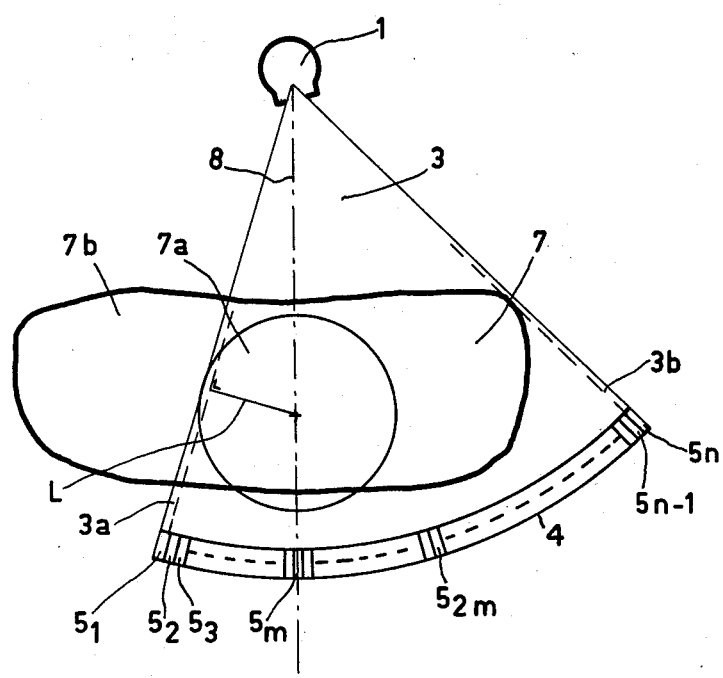
Figure 3A:
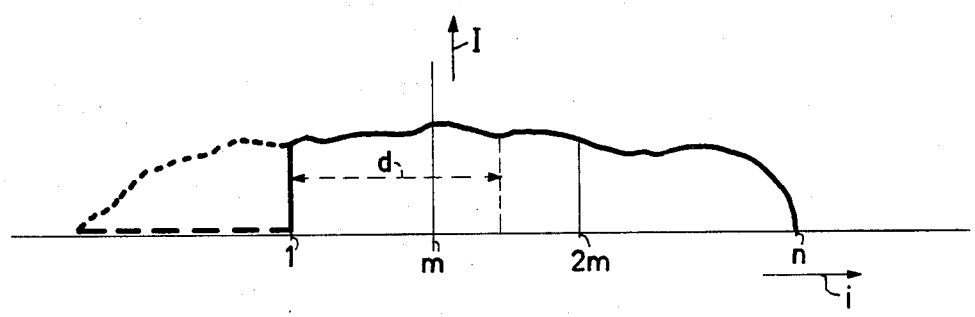

FIG. 2 shows a detail of FIG. 1 with the radiation source 1, the detector array 4 of separate detector elements $5_1, 5_2, \ldots 5_m, \ldots 5_{n-1}, 5_n$, and the asymmetrical positioning of the centre of rotation 9 with respect to the extreme measuring paths 3a and 3b of the radiation beam 3. It has been found that, if series of measuring signals determined in the situation shown is simply processed in known manner, artefacts in the form of bright and dark stripes appear in the reconstructed image. FIG. 3a shows a diagram of a profile measured by means of the arrangement shown in FIG. 2. The amplitudes I of the measuring signals are plotted one adjacent the other as a function of the position i of the detector element $5_i$ in the detector array 4. For the measuring signal with i=1, a transient occurs to the value 0. If a series of measuring signals comprising such a transient is convoluted, the transient is distributed as if it were over the entire reconstruction image. Obviously, the influence of the transient in a given position of the reconstruction image is proportional to the value of the convolution factor which is determined by the distance d (see FIG. 3a). Actually, instead of a series of measuring signals from a so-termed complete profile, only measuring signals of an unterrupted profile are processed. A complete profile is to be understood to mean the series of measuring signals which would be obtained if the part 7b of the object 7 which is now situated outside the X-ray beam 3 is also irradiated (FIG. 2) and the radiation passing therethrough is measured. FIG. 3a shows the interrupted, actually measured profile, the missing measuring signals being denoted by broken lines. It is to be noted that the number of measuring signals in a complete profile is substantially equal at the left and the right of the centre "m". During the further processing of the measuring signals, all missing measuring signals are assumed to be equal to zero for the convolution (denoted by a broken line in FIG. 3). This causes the transient and hence said artefacts.

In accordance with the invention, the measuring signals of an interrupted profile which are measured along measuring paths which extend through the centre 7a of the object 7 are adapted. The centre 7a is determined by the distance L between the centre of rotation 9 and the nearest extreme measuring path 3a. The measuring signals measured along measuring paths situated between the centre of rotation 9 and the extreme measuring path 3a (with the detectors $5_1, 5_2, \ldots 5_m$) are multiplied by a factor f which equals $\sin^2 (l.\pi/4.L)$, in which l is a distance between the measuring path associated with the measuring signal and the extreme measuring path 3a. The measuring signals measured along measuring paths which are mirrored relative to the centre line 8 with respect to the measuring paths between the centre of rotation 9 and the extreme measuring path 3a are multiplied by a complementary factor $(1-f)$. The measuring signals of the detector elements $5_1, 5_m$ and $5_{2m}$ are thus multiplied by 0, 0.5 and 1, respectively. The factors f and (1-f) is given in a table I for a computer tomography device comprising a total of 280 detectors, the centre line 8 extending through the centre of the detector element $5_{40}$ (m=40). It is clear that the factors for the measuring signals of the detector elements i and of the detector elements 80-i together have the value 1.

Figure 3B:
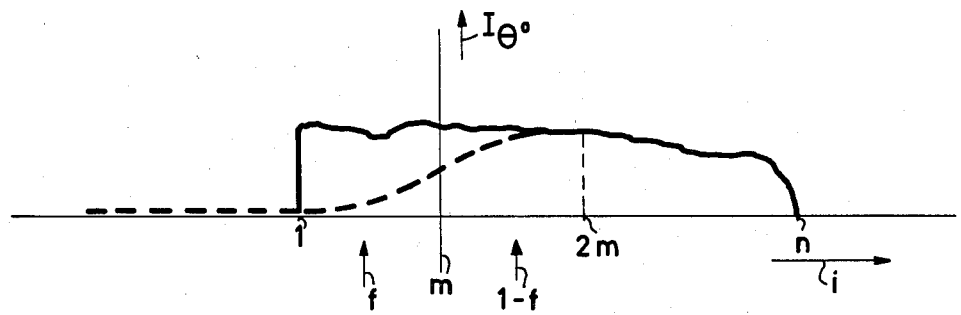
Figure 3C:
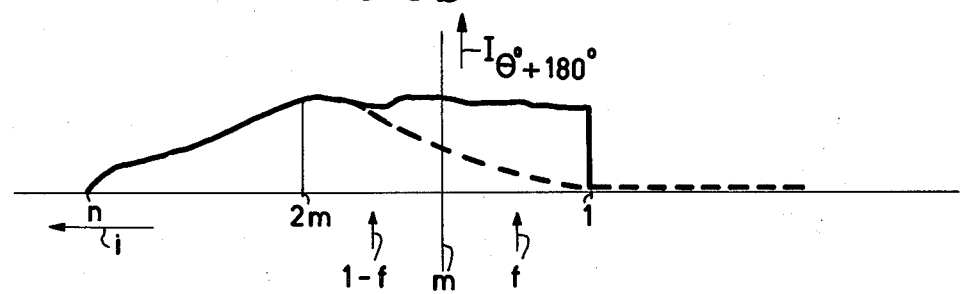

The reasons why the device in accordance with the invention produces reconstruction images without artefacts will be described hereinafter. The explanation can best be given on the basis of computer tomography involving image reconstruction with so-termed "parallel profiles". U.S. Pat. No. 3,983,398 describes how series of measuring signals determined by means of an arrangement similar to that shown in FIG. 2 can be used to compose profiles of measuring signals as if these signals were measured along adjacent, parallel extending measuring paths. A profile of this kind is shown in FIG. 3b, in which the measuring paths all enclose an angle θ with respect to, for example, the X-axis. FIG. 3c shows a second profile of measuring values where the associated measuring paths enclose an angle of 180°+θ° with respect to the X-axis (i.e. in the opposite direction with respect to the measuring values of the first profile). The measuring signals determined along measuring paths extending through the centre 7a are thus measured twice, i.e. by the detectors $5_1$ to $5_{2m}$. By adaptation of the measuring signals of both profiles in the described manner, the measuring signal in the one profile is multiplied by the factor f and the measuring signal measured along the same (oppositely directed) path in the other profile is multiplied by the factor 1-f (in the FIGS. 3b and c, the adapted measuring signals are denoted by broken lines), so that the sum of the measuring signals of the two profiles measured along the same path produces exactly one complete profile. A complete profile does not produce artefacts in the reconstructed image. The sum of the two interrupted profiles with the adapted measuring signals, therefore, does not produce artefacts either, because the operations to be executed, such as convolution and back projection which are performed separately on each profile are linear operations.

It will be clear that the adaptation of measuring signals can be achieved by adaptation of the gain factor of the amplifiers $14_1, 14_2, \ldots 14_n$ which are connected to the separate detector elements.

Figure 4:
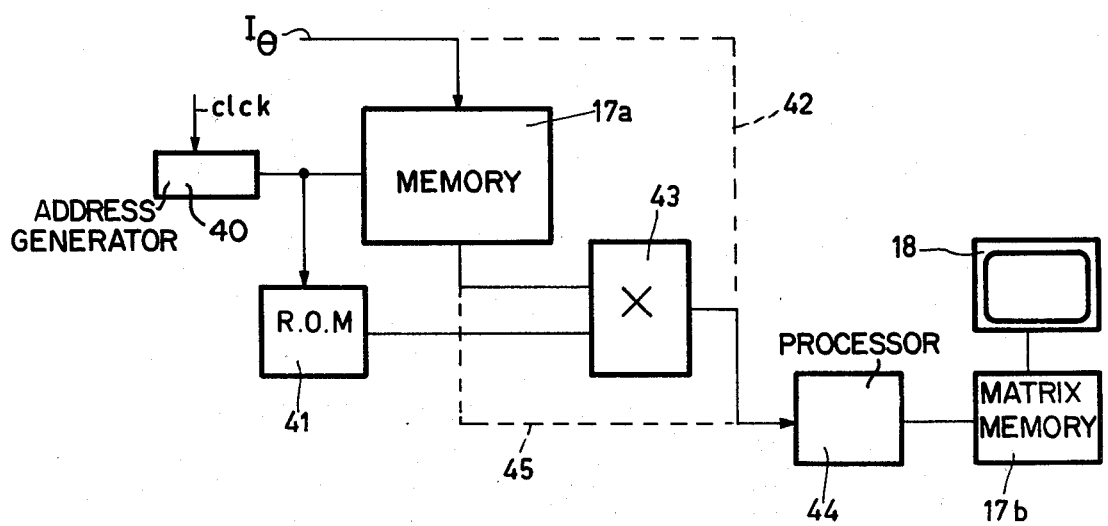

FIG. 4 shows a preferred embodiment of a part of the processing device of the device in accordance with the invention. Following a first irradiation from a first radiation source position, the logarithmated and digitized measuring signals obtained via the amplifiers $14_1 \ldots 14_n$ (now all having the same gain factor) and the signal converter are stored in a first section 17a of the memory 17. For the adaptation of the measuring signals, the processing device 16 comprises an address generator 40 which is actually a counter which counts the applied pulses clck, a read only memory (ROM) 41, and a multiplier circuit 43. The output of the address generator 40 is connected to an address input of the memory section 17a and the read only memory 41. After presentation of an address to the two address inputs, on the data output of the memory section 17a there is presented a measuring signal and on the data output of the read only memory 41 there is presented a factor f or 1-f, depending on the address or the detector number i of the detector element $5_i$ whereby the measuring signal stored at the address in the memory section 17a has been determined. The data outputs of the memories 17a and 41 are connected to the inputs of the multiplier circuit 43. The output of the multiplier circuit 43 is connected to a further section 44 of the processing device 16 which can start the convolution operation after the reception of all measuring signals of the first irradiation. The output of the multiplier circuit 43 can also be fed back to the memory section 17a (as denoted by broken lines 42), where all measuring signals of all irradiations can be stored. As is known, the processing of the adapted measuring signals by the processing device section 44 may commence before the complete number of irradiations has been executed. For the further processing, the adapted measuring values stored are applied directly (connection 45) to the further section 44 of the processing device 16. After convolution and back projection of the profiles with adapted measuring values by the section 44 of the processing device 16, the absorption values thus obtained are stored in a matrix memory 17b which forms part of the memory 17 of FIG. 1, after which the radiation absorption distribution obtained can be displayed on the monitor 18.

Because a fixed factor f or 1-f is assigned to each detector element, the measuring signals which originate from the detector elements and which are stored in the memory section 17 can simply be addressed by the same address as used for searching the factor f or 1-f.

As a result of the adaptation of measuring signals the effect of mechanical incorrect positioning and/or vibrations, being of major importance for the combining of two series of measuring values which have not been determined at the same instant, is greatly reduced; this is an important advantage.

TABLE I

| i | f | i | 1-f |
|---|---|---|---|
| 1 | 0.000385 | 79 | 0.999614 |
| 3 | 0.003466 | 77 | 0.996534 |
| 5 | 0.009607 | 75 | 0.990393 |
| 7 | 0.018772 | 73 | 0.981228 |
| 9 | 0.030904 | 71 | 0.969096 |
| 11 | 0.045928 | 69 | 0.954072 |
| 13 | 0.063752 | 67 | 0.936248 |
| 15 | 0.084265 | 65 | 0.915734 |
| 17 | 0.107342 | 63 | 0.892658 |
| 19 | 0.132893 | 61 | 0.867107 |
| 21 | 0.160600 | 59 | 0.839400 |
| 23 | 0.190453 | 57 | 0.809547 |
| 25 | 0.222215 | 55 | 0.777785 |
| 27 | 0.255689 | 53 | 0.744311 |
| 29 | 0.290670 | 51 | 0.709330 |
| 31 | 0.326942 | 49 | 0.673058 |
| 33 | 0.364280 | 47 | 0.635720 |
| 35 | 0.402455 | 45 | 0.597545 |
| 37 | 0.441231 | 43 | 0.558769 |
| 39 | 0.480370 | 41 | 0.519630 |
| 40 | 0.500000 | | |

What is claimed is:

1. A computed tomography device for determining a radiation absorption distribution in a plane of a body, comprising:
   radiation source means for generating a flat, fan-shaped beam of radiation which is situated in the plane and irradiates the body;
   detector means, which are rigidly connected to the source means, for detecting radiation from the source which has passed through the body and for supplying measuring signals which correspond to the intensity distribution of that radiation over a group of measuring paths which extend in a fan-like geometry from the radiation source;
   drive means which rotate the radiation source and the detector device around a center of rotation for irradiating the body from a multitude of radiation source positions, the center of rotation being asymmetrically situated with respect to the two extreme measuring paths at opposite edges of the group of measuring paths so that a first of the extreme paths is nearer to the center of rotation and the second extreme path is more distant from the center of rotation; and
   processing means for calculating, from the measuring signals, radiation absorption values associated with elements distributed as a matrix over the plane of the body; which include means for multiplying signals representative of radiation measured along a first group of radiation paths which are bounded by the radiation path passing through the center of rotation and the first extreme radiation path by factors f, the factor f having a value of 0.5 for the signal associated with the path passing through the center of rotation, having a value of 0 for the signal associated with the first extreme radiation path, and having values which decrease monotonically from the path passing through the center of rotation to the first extreme path and multiplying signals associated with paths which are symmetrically situated, about the center of rotation, from said first group of paths by corresponding complementary factors (1-f).

2. A device as claimed in claim 1 wherein the detector means comprises a plurality of separate detector elements whose positions define the positions of the measuring paths, wherein the means for multiplying comprise a like plurality of amplifiers each having an input connected to a corresponding detector element and a gain equal to the corresponding multiplying factor.

3. A method for operating a computed tomography device to determine a radiation absorption distribution in a plane of a body comprising the steps of:

irradiating the body with a flat, fan-shaped beam of radiation which is situated in the plane, from a plurality of radiation source positions which are distributed on a circle which surrounds the body;

measuring the intensity of radiation within the beam which has passed through the body along a group of measuring paths which extend in a fan-like manner from the radiation source, the two extreme measuring paths at the opposite edges of the group being asymmetrically situated with respect to the center of the circle so that a first extreme path is nearer to the center than the second path is, and supplying measuring signals representative of said intensity;

compensating values of the signals by multiplying signals representative of radiation measured along a first group of radiation paths which are bounded by the radiation path passing through the center and the first extreme radiation path by factors f, the factor f having a value of 0.5 for the signal associated with the path passing through the center, having a value of 0 for the signal associated with the first extreme radiation path, and having values which decrease monotonically from the path passing through the center to the first extreme path and multiplying signals associated with paths which are symmetrically situated, about the center, from said first group of paths by corresponding complementary factors (1-f); and processing the compensated values of the signals to determine a radiation absorption distribution in the plane.

4. A device as claimed in claims 1 or 2 or the method of claim 3 wherein the value of the factor f equals $\sin^2(l.\pi/4.L)$, wherein L is the distance between the center of rotation and the first extreme measuring path and l is a variable which is smaller than L and larger than 0 and is a measure of the distance from the associated measuring path to the first extreme measuring path.

* * * * *